US009486197B2

(12) United States Patent
Kleyman

(10) Patent No.: US 9,486,197 B2
(45) Date of Patent: *Nov. 8, 2016

(54) TWO-PART ACCESS ASSEMBLY

(71) Applicant: Covidien LP, Mansfield, MA (US)

(72) Inventor: Gennady Kleyman, Brooklyn, NY (US)

(73) Assignee: Covidien LP, Mansfield, MA (US)

(*) Notice: Subject to any disclaimer, the term of this patent is extended or adjusted under 35 U.S.C. 154(b) by 23 days.

This patent is subject to a terminal disclaimer.

(21) Appl. No.: 14/027,504

(22) Filed: Sep. 16, 2013

(65) Prior Publication Data

US 2014/0018632 A1 Jan. 16, 2014

Related U.S. Application Data

(63) Continuation of application No. 13/223,645, filed on Sep. 1, 2011, now Pat. No. 8,550,992.

(60) Provisional application No. 61/424,753, filed on Dec. 20, 2010.

(51) Int. Cl.
*A61B 17/02* (2006.01)
*A61B 17/34* (2006.01)

(52) U.S. Cl.
CPC ........ *A61B 17/0218* (2013.01); *A61B 17/3423* (2013.01); *A61B 17/3431* (2013.01); *A61B 2017/3429* (2013.01); *A61B 2017/3445* (2013.01); *A61B 2017/3466* (2013.01)

(58) Field of Classification Search
CPC .......... A61B 17/3423; A61B 17/0218; A61B 17/3431; A61B 2017/3429; A61B 2017/3445; A61B 2017/3466

USPC .......... 600/201–210, 114; 604/26, 204–208, 604/513, 264, 539; 606/1, 108, 213

See application file for complete search history.

(56) References Cited

U.S. PATENT DOCUMENTS

| 3,402,710 A | 9/1968 | Paleschuck |
| 4,016,884 A | 4/1977 | Kwan-Gett |
| 4,183,357 A | 1/1980 | Bentley et al. |
| 4,402,683 A | 9/1983 | Kopman |
| 4,863,438 A | 9/1989 | Gauderer et al. |
| 5,159,921 A | 11/1992 | Hoover |
| 5,242,415 A | 9/1993 | Kantrowitz et al. |

(Continued)

FOREIGN PATENT DOCUMENTS

| EP | 0538060 | 4/1993 |
| EP | 0950376 | 10/1999 |

(Continued)

OTHER PUBLICATIONS

European Search Report for corresponding EP11194227 date of mailing is Apr. 23, 2012 (7 pgs).

(Continued)

*Primary Examiner* — Pedro Philogene

(57) ABSTRACT

An assembly for accessing a body cavity through an opening in tissue is provided. The access assembly includes a flexible outer sleeve configured to be received through an opening in tissue. The outer sleeve defines a passageway therethrough. The access assembly further includes an inner core configured for selective reception within the passageway of the outer sleeve. The inner core defines at least a first lumen configured to receive a surgical instrument therethrough.

10 Claims, 6 Drawing Sheets

(56) References Cited

U.S. PATENT DOCUMENTS

| | | | |
|---|---|---|---|
| 5,366,478 A | 11/1994 | Brinkerhoff et al. | |
| 5,375,588 A | 12/1994 | Yoon | |
| 5,391,156 A | 2/1995 | Hildwein et al. | |
| 5,437,683 A | 8/1995 | Neumann et al. | |
| 5,460,170 A | 10/1995 | Hammerslag | |
| 5,480,410 A | 1/1996 | Cuschieri et al. | |
| 5,490,843 A | 2/1996 | Hildwein et al. | |
| 5,514,133 A | 5/1996 | Golub et al. | |
| 5,522,791 A | 6/1996 | Leyva | |
| 5,524,644 A | 6/1996 | Crook | |
| 5,545,179 A | 8/1996 | Williamson, IV | |
| 5,556,385 A | 9/1996 | Andersen | |
| 5,634,937 A | 6/1997 | Mollenauer et al. | |
| 5,649,550 A | 7/1997 | Crook | |
| 5,653,705 A | 8/1997 | de la Torre et al. | |
| 5,672,168 A | 9/1997 | de la Torre et al. | |
| 5,728,103 A | 3/1998 | Picha et al. | |
| 5,741,298 A | 4/1998 | MacLeod | |
| 5,803,921 A | 9/1998 | Bonadio | |
| 5,813,409 A | 9/1998 | Leahy et al. | |
| 5,830,191 A | 11/1998 | Hildwein et al. | |
| 5,906,577 A | 5/1999 | Beane et al. | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,990,382 A | 11/1999 | Fox | |
| 6,017,355 A | 1/2000 | Hessel et al. | |
| 6,018,094 A | 1/2000 | Fox | |
| 6,024,736 A | 2/2000 | de la Torre et al. | |
| 6,033,426 A | 3/2000 | Kaji | |
| 6,033,428 A | 3/2000 | Sardella | |
| 6,077,288 A | 6/2000 | Shimomura et al. | |
| 6,110,154 A | 8/2000 | Shimomura et al. | |
| 6,142,936 A | 11/2000 | Beane et al. | |
| 6,241,768 B1 | 6/2001 | Agarwal et al. | |
| 6,254,534 B1 | 7/2001 | Butler et al. | |
| 6,315,770 B1 | 11/2001 | de la Torre et al. | |
| 6,319,246 B1 | 11/2001 | de la Torre et al. | |
| 6,382,211 B1 | 5/2002 | Crook | |
| 6,440,063 B1 | 8/2002 | Beane et al. | |
| 6,450,983 B1 | 9/2002 | Rambo | |
| 6,454,783 B1 | 9/2002 | Piskun | |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,814,078 B2 | 11/2004 | Crook | |
| 6,840,951 B2 | 1/2005 | de la Torre et al. | |
| 6,846,287 B2 | 1/2005 | Bonadio et al. | |
| 6,916,310 B2 | 7/2005 | Sommerich | |
| 6,916,331 B2 | 7/2005 | Mollenauer et al. | |
| 6,939,296 B2 | 9/2005 | Ewers et al. | |
| 6,945,932 B1 | 9/2005 | Caldwell et al. | |
| 6,958,037 B2 | 10/2005 | Ewers et al. | |
| 6,972,026 B1 | 12/2005 | Caldwell et al. | |
| 7,008,377 B2 | 3/2006 | Beane et al. | |
| 7,033,319 B2 | 4/2006 | Pulford et al. | |
| 7,052,454 B2 | 5/2006 | Taylor | |
| 7,101,353 B2 | 9/2006 | Lui et al. | |
| 7,153,261 B2 | 12/2006 | Wenchell | |
| 7,163,510 B2 | 1/2007 | Kahle et al. | |
| 7,195,590 B2 | 3/2007 | Butler et al. | |
| 7,214,185 B1 | 5/2007 | Rosney et al. | |
| 7,238,154 B2 | 7/2007 | Ewers et al. | |
| 7,300,399 B2 | 11/2007 | Bonadio et al. | |
| 7,331,940 B2 | 2/2008 | Sommerich | |
| 7,344,547 B2 | 3/2008 | Piskun | |
| 7,377,898 B2 | 5/2008 | Ewers et al. | |
| 7,393,322 B2 | 7/2008 | Wenchell | |
| 7,445,597 B2 | 11/2008 | Butler et al. | |
| 7,473,221 B2 | 1/2009 | Ewers et al. | |
| 7,481,765 B2 | 1/2009 | Ewers et al. | |
| 7,540,839 B2 | 6/2009 | Butler et al. | |
| 7,559,893 B2 | 7/2009 | Bonadio et al. | |
| 7,608,082 B2 | 10/2009 | Cuevas et al. | |
| 7,650,887 B2 | 1/2010 | Nguyen et al. | |
| 7,704,207 B2 | 4/2010 | Albrecht et al. | |
| 7,717,847 B2 | 5/2010 | Smith | |
| 7,727,146 B2 | 6/2010 | Albrecht et al. | |
| 7,736,306 B2 | 6/2010 | Brustad et al. | |
| 7,766,824 B2 | 8/2010 | Jensen et al. | |
| 7,815,567 B2 | 10/2010 | Albrecht et al. | |
| 7,837,612 B2 | 11/2010 | Gill et al. | |
| 7,867,164 B2 | 1/2011 | Butler et al. | |
| 7,909,760 B2 | 3/2011 | Albrecht et al. | |
| 7,951,076 B2 | 5/2011 | Hart et al. | |
| 7,998,068 B2 | 8/2011 | Bonadio et al. | |
| 8,343,047 B2 * | 1/2013 | Albrecht et al. | 600/206 |
| 8,353,824 B2 | 1/2013 | Shelton, IV et al. | |
| 8,550,992 B2 * | 10/2013 | Kleyman | A61B 17/3423 600/206 |
| 8,602,983 B2 * | 12/2013 | Kleyman | A61B 17/3423 600/208 |
| 2001/0037053 A1 | 11/2001 | Bonadio et al. | |
| 2003/0014076 A1 | 1/2003 | Mollenauer et al. | |
| 2004/0092795 A1 | 5/2004 | Bonadio et al. | |
| 2004/0111061 A1 | 6/2004 | Curran | |
| 2004/0267096 A1 | 12/2004 | Caldwell et al. | |
| 2005/0020884 A1 | 1/2005 | Hart et al. | |
| 2005/0096695 A1 | 5/2005 | Olich | |
| 2005/0148823 A1 | 7/2005 | Vaugh et al. | |
| 2005/0192483 A1 | 9/2005 | Bonadio et al. | |
| 2006/0071432 A1 | 4/2006 | Staudner | |
| 2006/0149137 A1 | 7/2006 | Pingleton et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0241651 A1 | 10/2006 | Wilk | |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247678 A1 | 11/2006 | Weisenburgh et al. | |
| 2006/0270911 A1 | 11/2006 | Voegele et al. | |
| 2007/0118175 A1 | 5/2007 | Butler et al. | |
| 2007/0151566 A1 | 7/2007 | Kahle et al. | |
| 2007/0203398 A1 | 8/2007 | Bonadio et al. | |
| 2007/0208312 A1 | 9/2007 | Norton et al. | |
| 2007/0270654 A1 | 11/2007 | Pignato et al. | |
| 2007/0270882 A1 | 11/2007 | Hjelle et al. | |
| 2008/0027476 A1 | 1/2008 | Piskun | |
| 2008/0097162 A1 | 4/2008 | Bonadio et al. | |
| 2008/0200767 A1 | 8/2008 | Ewers et al. | |
| 2009/0036745 A1 | 2/2009 | Bonadio et al. | |
| 2009/0093752 A1 | 4/2009 | Richard et al. | |
| 2009/0093850 A1 | 4/2009 | Richard | |
| 2009/0137879 A1 | 5/2009 | Ewers et al. | |
| 2009/0187079 A1 | 7/2009 | Albrecht et al. | |
| 2009/0204067 A1 | 8/2009 | Abu-Halawa | |
| 2009/0221968 A1 | 9/2009 | Morrison et al. | |
| 2009/0326332 A1 | 12/2009 | Carter | |
| 2010/0063452 A1 | 3/2010 | Edelman et al. | |
| 2010/0100043 A1 | 4/2010 | Racenet | |
| 2010/0240960 A1 * | 9/2010 | Richard | 600/208 |
| 2010/0249523 A1 | 9/2010 | Spiegal et al. | |
| 2010/0249524 A1 | 9/2010 | Ransden et al. | |
| 2010/0262080 A1 | 10/2010 | Shelton | |
| 2010/0286484 A1 * | 11/2010 | Stellon et al. | 600/208 |
| 2010/0298646 A1 * | 11/2010 | Stellon et al. | 600/208 |
| 2010/0312063 A1 | 12/2010 | Hess | |
| 2010/0312065 A1 * | 12/2010 | Shelton et al. | 600/207 |
| 2011/0009704 A1 | 1/2011 | Marczyk et al. | |
| 2011/0021877 A1 | 1/2011 | Fortier et al. | |
| 2011/0028891 A1 | 2/2011 | Okoniewski | |
| 2011/0034778 A1 | 2/2011 | Kleyman | |
| 2011/0054257 A1 * | 3/2011 | Stopek | 600/206 |
| 2011/0054258 A1 | 3/2011 | O'Keefe et al. | |
| 2011/0082341 A1 | 4/2011 | Kleyman et al. | |
| 2011/0082343 A1 | 4/2011 | Okoniewski | |

(56) References Cited

U.S. PATENT DOCUMENTS

| | | |
|---|---|---|
| 2011/0082346 A1 | 4/2011 | Stopek |
| 2012/0130191 A1* | 5/2012 | Pribanic .................. 600/208 |

FOREIGN PATENT DOCUMENTS

| | | |
|---|---|---|
| EP | 1312318 | 5/2003 |
| EP | 2044889 | 4/2009 |
| EP | 2095781 | 9/2009 |
| EP | 2098182 | 9/2009 |
| EP | 2181657 | 5/2010 |
| EP | 2229900 | 9/2010 |
| EP | 2238924 | 10/2010 |
| EP | 2238925 | 10/2010 |
| EP | 2248478 | 11/2010 |
| EP | 2253283 | 11/2010 |
| EP | 2272450 | 1/2011 |
| EP | 2277464 | 1/2011 |
| EP | 2292165 | 3/2011 |
| WO | WO 96/36283 | 11/1996 |
| WO | WO 01/08581 | 2/2001 |
| WO | WO 01/32116 | 5/2001 |
| WO | WO 01/32120 | 5/2001 |
| WO | WO 03/034908 | 5/2003 |
| WO | WO 2004/043275 | 5/2004 |
| WO | WO 2004/054456 | 7/2004 |
| WO | WO 2004/075741 | 9/2004 |
| WO | WO 2006/110733 | 10/2006 |
| WO | WO 2008/103151 | 8/2008 |
| WO | WO 2009/036343 | 3/2009 |

OTHER PUBLICATIONS

Japanese Office Action dated Jul. 31, 2015 issued in connection with Japanese Patent Application No. 2011-271719.
Japanese Laid-Open Publication No. 2008-125819 (abstract only).
Japanese Office Action dated Mar. 3, 2016 in corresponding JP Application No. 2011-271719.

* cited by examiner

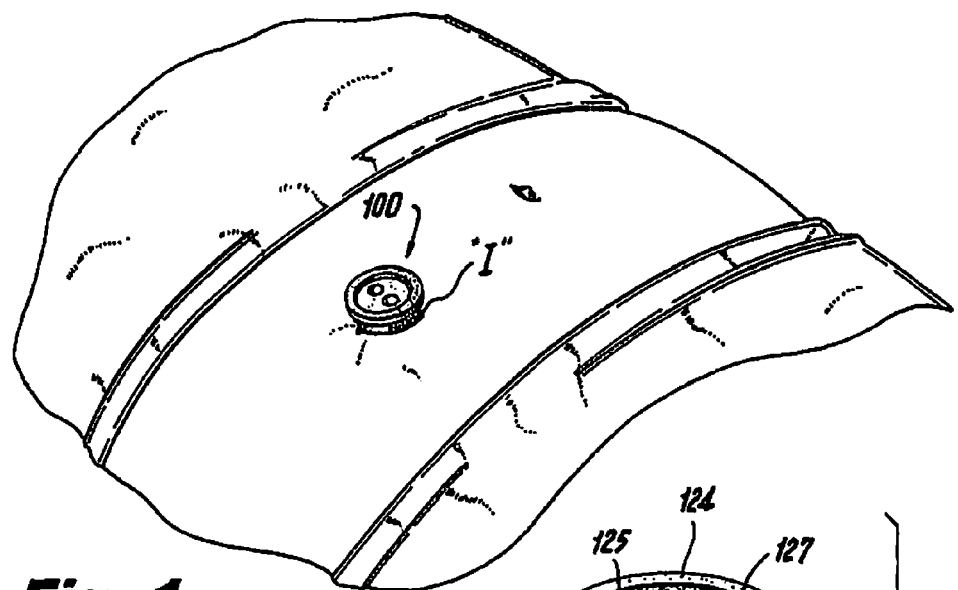
Fig. 1
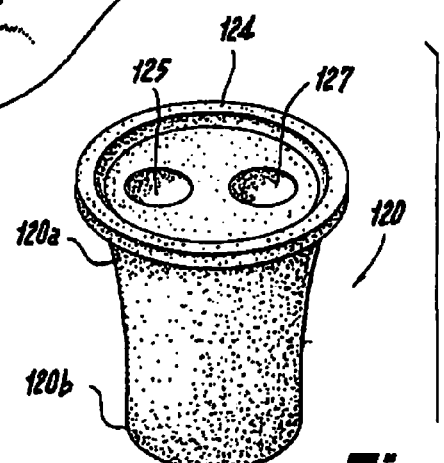
Fig. 3
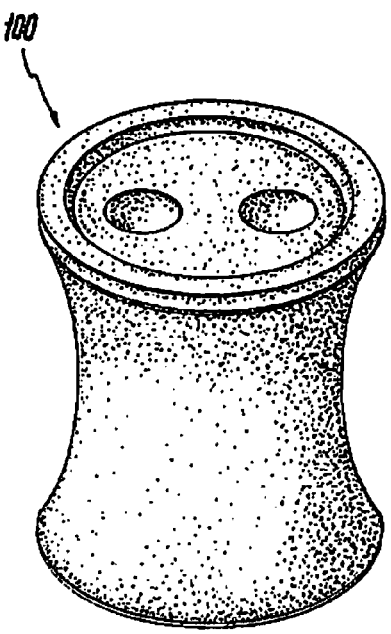
Fig. 2
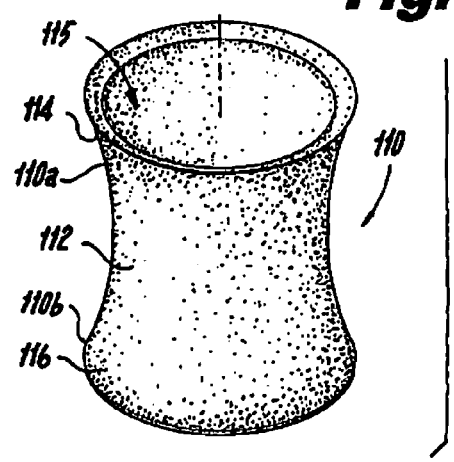

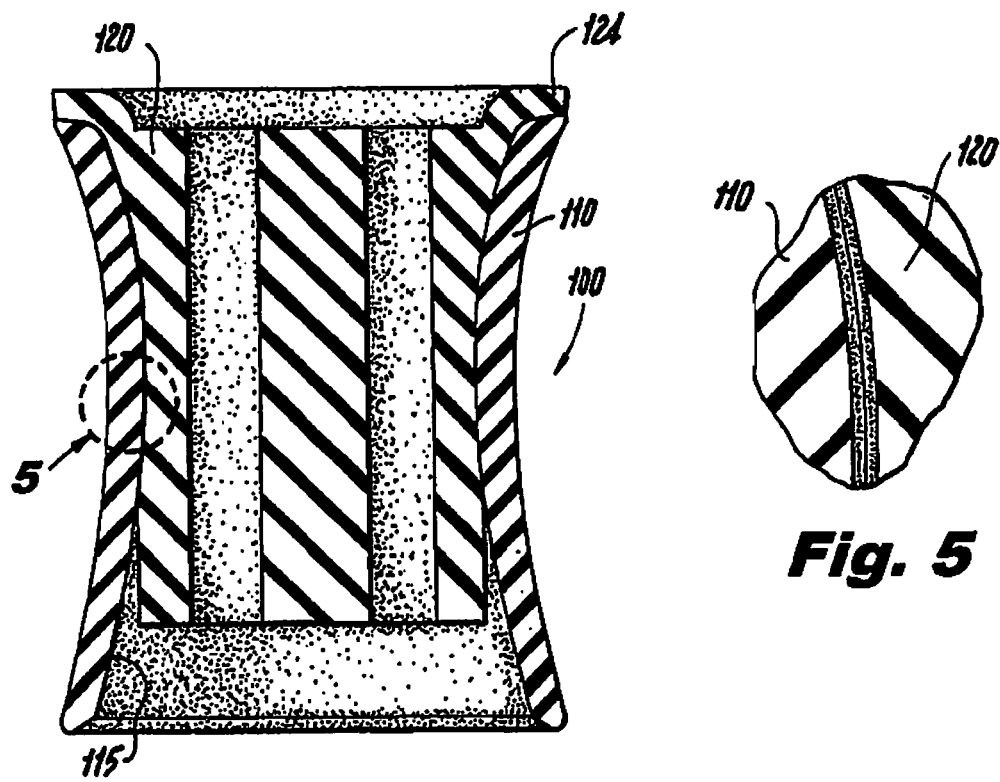
Fig. 4
Fig. 5
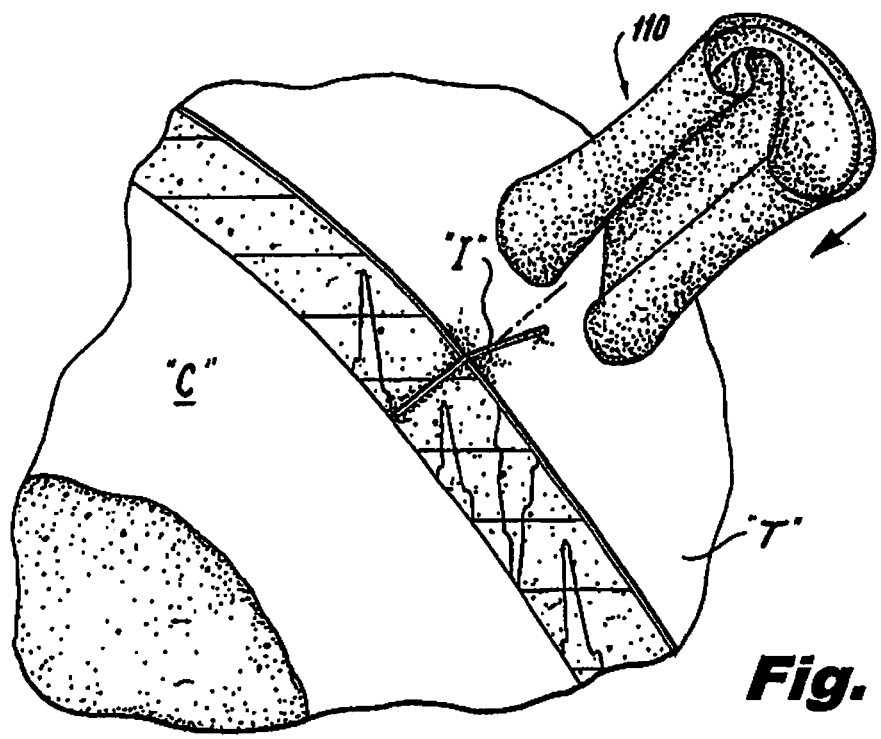
Fig. 6

TWO-PART ACCESS ASSEMBLY

CROSS-REFERENCE TO RELATED APPLICATIONS

This application is a continuation of U.S. application Ser. No. 13/223,645 filed Sep. 1, 2011, now U.S. Pat. No. 8,550,992, which claims benefit of Provisional application No. 61/424,753 filed Dec. 20, 2010, and the disclosures of each of the above-identified applications are hereby incorporated by reference in their entirety.

BACKGROUND

1. Technical Field

The present disclosure relates to access assemblies for use in surgical procedures. More particularly, the present disclosure relates to a two-part flexible access assembly.

2. Background of Related Art

Access assemblies configured for reception through an opening or incision into an body cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing located on the proximal end of the cannula to access the body cavity in a sealing manner.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, e.g., forceps. Compression of the assembly reduces the profile of the assembly, thereby facilitating reception of the assembly into the incision. Upon release of the compressive force, the compressed assembly returns to an uncompressed configuration.

Applying a compressive force to the compressive access assemblies, whether by hand or using an insertion device, excessive handling may damage the assembly. Additionally, maintaining the compressive force on the access assembly during installation and reapplying the compressive force during removal of the access assembly may result in damage to surrounding tissue.

Therefore, it is desirable to provide a compressible access assembly which is capable of being received through an opening and removed therefrom with limited compressive force.

SUMMARY

The present invention, according to various embodiments thereof, may relate to an access assembly comprising a flexible outer sleeve configured to be received through an opening in tissue, the outer sleeve defining a passageway therethrough; and an inner core configured for selective reception within the passageway of the outer sleeve, the inner core defining at least a first lumen configured to receive a surgical instrument therethrough. The outer sleeve may define a substantially hour-glass shape. In an embodiment, at least one of the outer sleeve and inner core may be composed of at least one of silicone, thermoplastic elastomers (TPE), rubber, foam, gel. The inner core may include three lumen and/or a longitudinal notch and/or at least one valve assembly. The opening in the tissue may be an incision or a natural orifice. The inner core may be externally threaded to provide a more secure engagement with the outer sleeve.

In another embodiment, the present invention may relate to a method of accessing a body cavity, the method comprising the steps of: providing an access assembly having an outer sleeve and an inner core; compressing the outer sleeve to permit reception of the outer sleeve through an opening in tissue; inserting the compressed outer sleeve through tissue; permitting the compressed outer sleeve to decompress within the opening; inserting the inner core into the outer sleeve to cause decompression of the outer sleeve and to create seal within the opening; and manipulating one or more instruments through the access assembly to complete a procedure. The method may also include the step of creating an incision in tissue for access to the body cavity.

DESCRIPTION OF THE DRAWINGS

Embodiments of a flexible access assembly are disclosed herein with reference to the drawings, wherein:

FIG. 1 is a perspective view of an embodiment of an access assembly according to the present disclosure received through an incision in the abdominal wall of a patient;

FIG. 2 is an enlarged perspective view of the access assembly of FIG. 1;

FIG. 3 is an exploded perspective view of the access assembly of FIGS. 1 and 2;

FIG. 4 is a cross-sectional side view of the access assembly of FIGS. 1-3;

FIG. 5 is an enlarged view of portion 5 of FIG. 4;

FIGS. 6-11 illustrate the use the access assembly of FIGS. 1-5;

DETAILED DESCRIPTION

Figure 7:
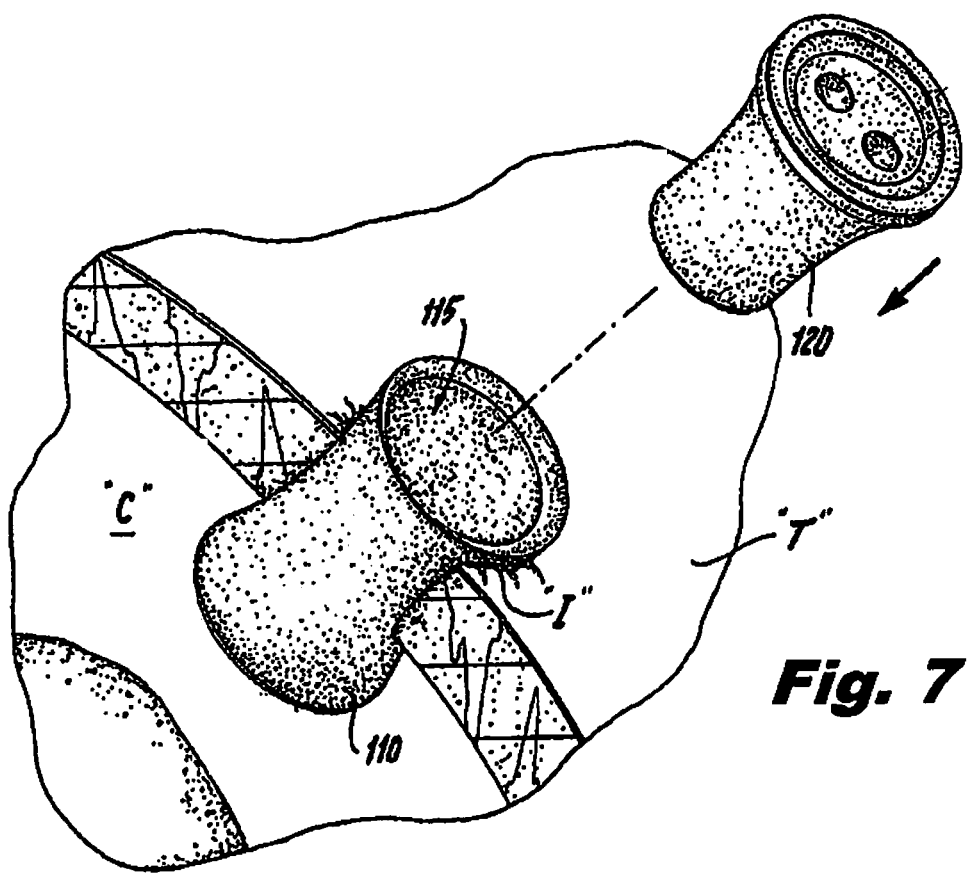

Embodiments of the presently disclosed access assembly will now be described in detail with reference to the drawings wherein like numerals designate identical or corresponding elements in each of the several views. As is common in the art, the term "proximal" refers to that part or component closer to the user or operator, e.g. surgeon or physician, while the term "distal" refers to that part or component further away from the user. Although the access assemblies of the present disclosure will be described as relates to accessing an abdominal cavity through an incision in the abdominal wall, the access assemblies of the present disclosure may be modified for use in other closed procedures, e.g., laparoscopic, arthroscopic, endoscopic. Furthermore, the access assemblies of the present disclosure may be modified for use in accessing internal cavities through natural orifices, e.g., anus, vagina.

Referring initially to FIG. 1, a two-part access assembly according to an embodiment of the present disclosure is shown generally as access assembly 100. Access assembly 100 is configured for insertion through an opening in tissue, e.g., an incision, such that after insertion, access assembly 100 creates a seal within the opening through which a surgeon may insert and manipulate one or more surgical instruments to complete a procedure.

With reference to FIGS. 1-4, access assembly 100 includes an outer sleeve 110 and an inner core 120. Outer sleeve 110 and inner core 120 may be formed of various materials, such as, for example, silicone, thermoplastic elastomers (TPE), rubber, foam, gel, etc. Outer sleeve 110 and inner core 120 may be constructed from the same or different materials. In one embodiment, each of sleeve 110 and core 120 includes a TPE material that is infused with an inert gas, e.g. $CO_2$ or Nitrogen, to form a foam structure. Either or both of sleeve 110 and core 120 may be coated (FIG. 5) with a lubricant, e.g. Parylene N or C, in order to create a lubricious surface. Various other coatings, e.g., hydrophilic, hydrophobic, bio-agents, anti-infection, analgesic, may also be employed to improve the characteristics of access assembly 100 or to adapt access assembly 100 for a specific procedure.

With particular reference now to FIGS. 2-4, outer sleeve 110 of access assembly 100 defines a substantially hourglass shape when viewed from the side. Outer sleeve 110 includes a central portion 112 having an upper rim 114 located at a proximal end 110a thereof and a lower rim 116 located at a distal end 110b thereof. Central portion 112 is configured to span the thickness of tissue "T" (FIG. 6). Upper rim 114 and lower rim 116 aid in preventing movement of access assembly 100 longitudinally through incision "I" upon reception of access assembly 100 being properly received therethrough. As the thickness of tissue depends on the body composition of the patient and the location through which the underlying cavity is being accessed, the length and size of access assembly 100, generally, and outer sleeve 110, specifically, may be modified to suit a given procedure. In this manner, an adult patient having fatty abdominal tissue requires an access assembly having a longer central portion 112 then an access assembly sized for an infant.

With reference still to FIGS. 2-4, outer sleeve 110 defines a passageway 115 extending therethrough. As shown, passageway 115 defines a substantially hourglass shape corresponding the shape of outer sleeve 110. Alternatively, passageway 115 may be conical, tapered, stepped or otherwise configured to facilitate reception of inner core 120 therein. Passageway 115 is configured to at least partially receive inner core 120 therein. As shown, outer sleeve 110 is configured such that a rim 124 formed on a proximal end 120a of inner core 120 is maintained proximal of upper rim 114 when inner core 120 is joined with outer sleeve 110. Alternatively, outer sleeve 110 is configured such that rim 124 of inner core 120 is maintained flush with upper rim 114 of outer sleeve 110 or recessed within passageway 115 of outer sleeve 110. Outer sleeve 110 may include a locking mechanism, for example, a flange or recess (not shown), configured to engage a corresponding recess or flange (not shown) formed on inner core 120 to more secure engage outer sleeve 110 and inner core 120.

Still referring to FIGS. 2-4, inner core 120 of access assembly 100 includes a compressible body configured to be received within passageway 115 of outer sleeve 110. Inner core 120 includes proximal and distal ends 120a, 120b, respectively. Distal end 120b of inner core 120 is configured to be received within passageway 115 of outer sleeve 110. As discussed above, proximal end 120a of inner core 120 includes a rim 124 and may be configured to abut, lay flush with or be recessed with respect to upper rim 114 of outer sleeve 110 when inner core 120 is received within passageway 115 of outer sleeve 110. Inner core 120 defines a plurality of lumen 125, 127. As shown, inner core 120 includes two lumens 125, 127 having substantially similar size and shape for receiving instruments of substantially similar diameter. Alternatively, lumens 125, 127 may have different sizes and/or shapes for receiving instruments of different configurations. In one embodiment, inner core 120 defines a single lumen (FIG. 9) for receiving a single, large instrument. Lumens 125, 127 extend through inner core 120 and define longitudinal axes configured to receive surgical instruments, cannula assemblies, a valve assemblies and/or insufflation apparatus in a sealed manner. Either or both of lumens 125, 127 may include a valve assembly (FIG. 14) to permit sealed reception of an instrument therethrough. Lumens 125, 127 may include a protective lining extending along any or all of the length thereof to prevent tearing of inner core 120 as instruments "D1", "D2" (FIG. 9) are manipulated therethrough. Lumens 125, 127 may also be coated with a lubricant to assist in insertion of surgical instruments therethrough.

The use of access assembly 100 will now be described with reference to FIGS. 6-11. The following discussion will include using access assembly 100 for accessing a body cavity "C" through an incision "I". As discussed above, access assembly 100 may be used for accessing other cavities or lumen through other openings, including naturally orifices, e.g., anus.

Referring initially to FIG. 6, an incision "I" is created in tissue "T" through which access assembly 100 will be inserted to access body cavity "C". If not provided separate from inner core 120, outer sleeve 110 is separated from inner core 120. Outer sleeve 110 is then laterally compressed to permit passage of outer sleeve through incision "I".

Turning to FIG. 7, once received through incision "I", outer sleeve 110 is permitted to return to an initial, uncompressed condition. Outer sleeve 110 may only partially uncompress within incision "I" because of the force of tissue "T" against outer sleeve 110. Distal end 120 of inner core 120 is then inserted within passageway 115 of outer sleeve 110 as outer sleeve 110 is maintained within incision "I" in tissue "T".

Figure 8:
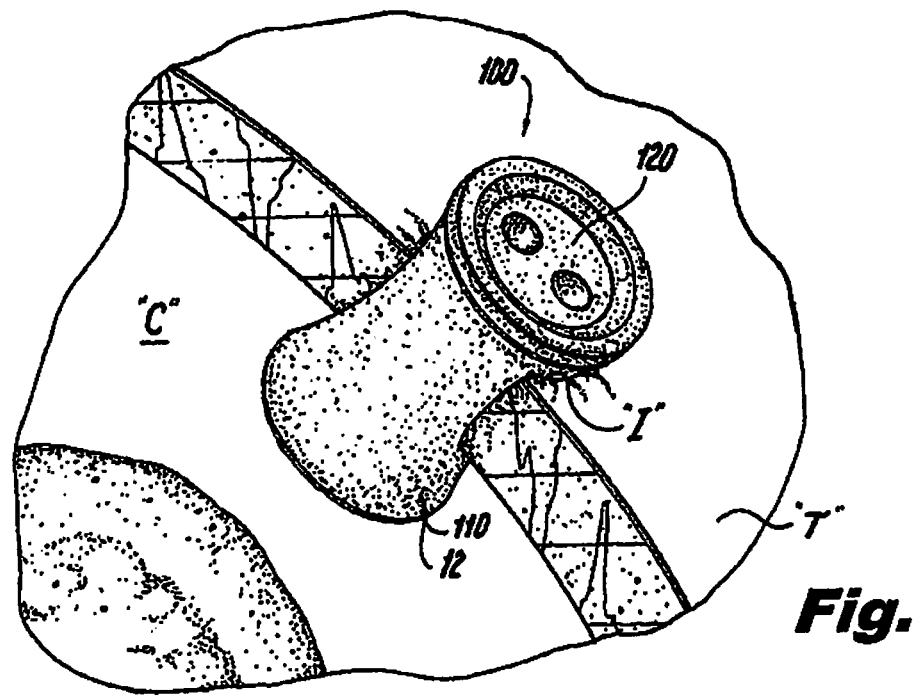

With reference to FIG. 8, insertion of inner core 120 within outer sleeve 110 causes sleeve 110 to return to the initial, uncompressed condition. In one embodiment, the tapered, conical shape of distal end 120b of inner core 120 assists in decompression of outer sleeve 110. In some embodiments, inner core 120 may be sized to further expand outer sleeve 110. Decompression or expansion of outer sleeve 110 creates a seal between outer sleeve 110 and tissue "T" to prevent escape of insufflation gas through incision "I". As discussed above, outer sleeve 110 and inner core 120 are also configured to form a seal therebetween to prevent the escape of insufflation gas from body cavity "C".

Figure 9:
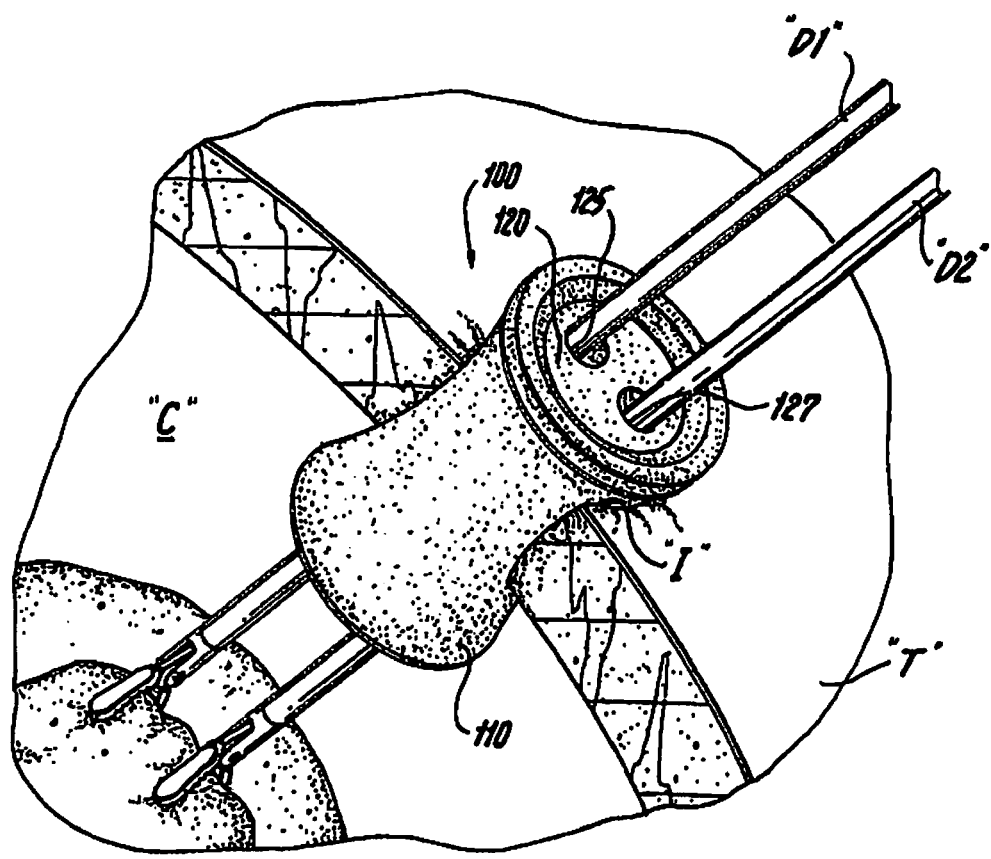
Figure 10:
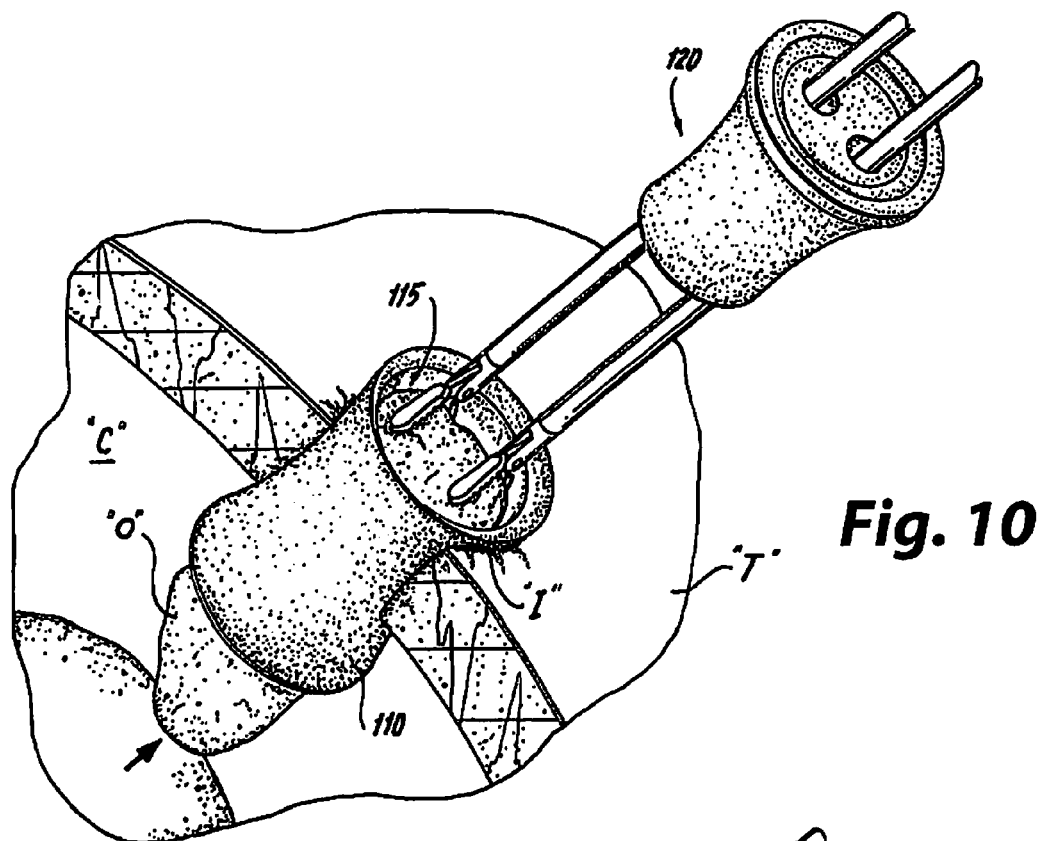
Figure 11:
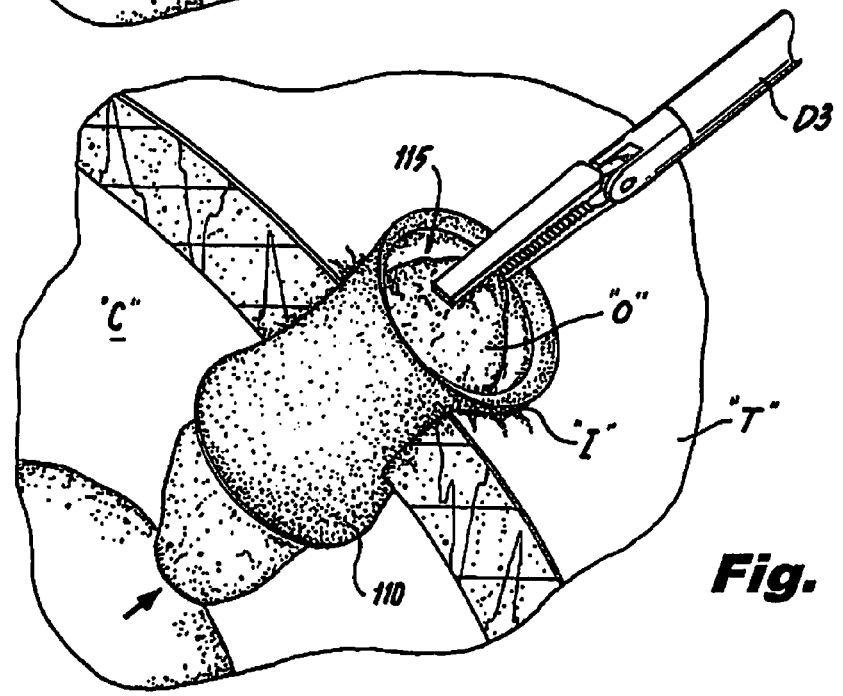

Turning to FIG. 9, once inner core 120 is received with outer sleeve 110, access assembly 100 operates in a traditional manner. Each of lumen 25, 27 are configured to receive one or more surgical devices "D1", D2" (FIG. 10), "D3" (FIG. 11). During a procedure, it is envisioned that inner core 120 may be separated from outer sleeve 110 to permit the removal of an organ "O" or other tissue. As seen in FIG. 10, surgical devices "D1", "D2" may remain inserted through inner core 120 as inner core 120 is separated from outer sleeve 110 to permit the removal of organ "O". Alternatively, and as seen in FIG. 11, inner core 120 may be completely removed from outer sleeve 110 to permit removal of organ "O". Removal of core 120 further permits the passage of larger instruments into cavity "C" through access assembly 100. While positioned through incision "I" in tissue "T", access assembly 100 may be used to complete any number of procedures.

Removal of access assembly 100 from within incision "I" occurs in the reverse order of insertion. Inner core 120 is initially separated from outer sleeve 110. Outer sleeve 110 is then compressed to permit retraction from incision "I". Alternatively, both inner core 120 and outer sleeve 110 may be compressed simultaneously such that access assembly 100 may be removed as a single unit. Once access assembly 100 is removed from incision "I", incision "I" is closed in a conventional manner.

Figure 14:
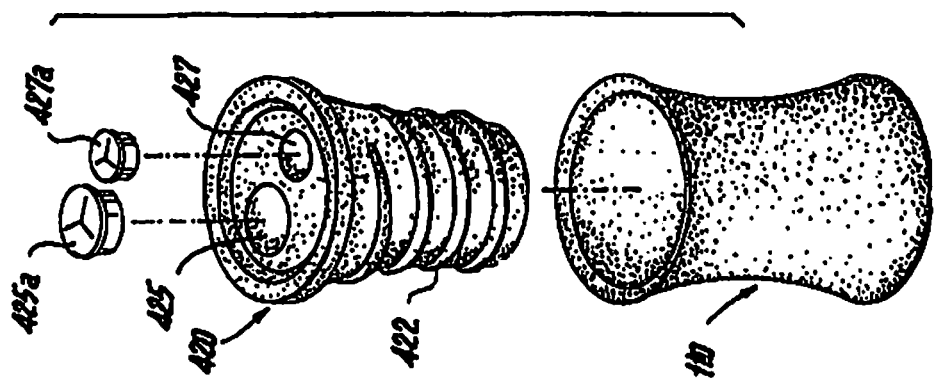
FIG. 14 is an exploded perspective view of an access assembly according to still yet another embodiment of the present disclosure.
Figure 13:
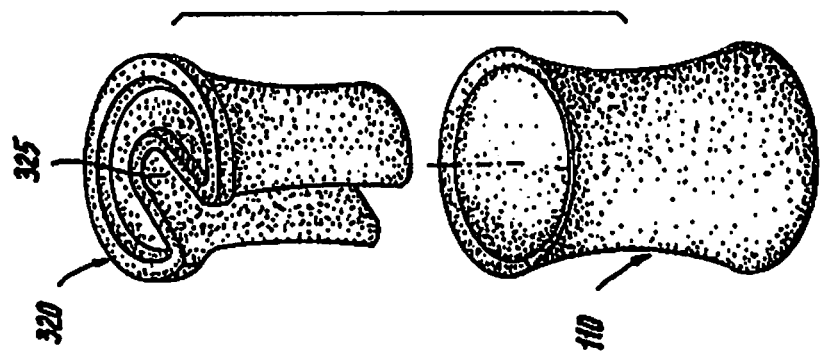
FIG. 13 is an exploded perspective view of an access assembly according to yet another embodiment of the present disclosure.
Figure 12:
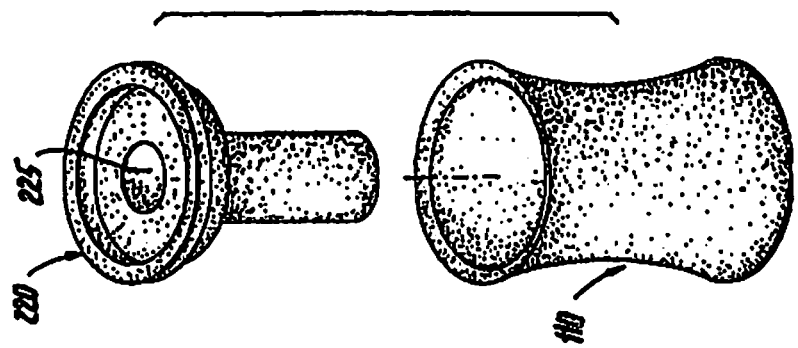
FIG. 12 is an exploded perspective view of an access assembly according to another embodiment of the present disclosure.

Turning now to FIGS. 12-14, alternative embodiments of inner cores for use with the presently disclosed access assembly are shown. As seen in FIG. 12, inner core 220 may include a single lumen 225 configured to permit greater movement of a surgical device "D3" (FIG. 11). As seen in FIG. 13, inner core 320 may include a longitudinally extending notch 325 inserted therethrough configured to permit reception of a non-circular instrument therethrough in a sealed manner. In another embodiment, as seen in FIG. 14, inner core 420 may include an outer thread 422 configured for more secure engagement with outer sleeve 110. Inner core 420 further includes a pair of lumen 425, 427 each including respective valve assemblies 425a, 427a. Each of valve assemblies 425a, 426a are configure to receive a surgical device in a sealed manner. Each of lumen 425, 427 may be of the same diameter, or different diameters, as shown.

It will be understood that various modifications may be made to the embodiments disclosed herein. For example, either of the inner core or outer sleeve may have a groove or lip, and the other of the inner core or outer sleeve may have a corresponding lip or groove, and the groove of one is configured to engage the lip of the other to more securely join the inner core with the outer sleeve. Therefore, the above description should not be construed as limiting, but merely as exemplifications of particular embodiments. Those skilled in the art will envision other modifications within the scope and spirit of the claims appended hereto.

The invention claimed is:

1. An access assembly comprising:
   an outer sleeve configured to be received through an opening in tissue, the outer sleeve defining a passageway therethrough; and
   an inner core selectively positionable within the passageway of the outer sleeve, the inner core defining a lumen configured to receive a surgical instrument therethrough, wherein the inner core is formed of foam and is transitionable between an expanded state and a compressed state, at least a portion of the outer sleeve or the inner core including a lubricious surface to translatably insert the inner core into the passageway of the outer sleeve.

2. The access assembly according to claim 1, wherein the outer sleeve comprises at least one of silicone, thermoplastic elastomers, rubber, foam, or gel.

3. The access assembly according to claim 1, wherein the outer sleeve defines a substantially hour-glass shape.

4. The access assembly according to claim 1, wherein the outer sleeve is transitionable between an uncompressed condition and a compressed condition.

5. The access assembly according to claim 4, wherein the passageway of the outer sleeve includes a first diameter when the outer sleeve is in the uncompressed condition and the inner core defines a second diameter when the inner core is in the expanded state, the second diameter larger than the first diameter.

6. The access assembly according to claim 1, wherein the outer sleeve includes a central portion having a proximal rim and a distal rim.

7. The access assembly according to claim 1, wherein the inner core includes a valve assembly configured for sealed reception of the surgical instrument inserted therethrough.

8. The access assembly according to claim 1, wherein the inner core includes a portion having a tapered configuration.

9. The access assembly according to claim 1, wherein the inner core defines at least one longitudinal notch.

10. The access assembly according to claim 9, wherein the at least one longitudinal notch is in communication with an inner surface of the outer sleeve when the inner core is disposed at least partially within the passageway of the outer sleeve.

* * * * *